United States Patent
Scoville et al.

(12) 
(10) Patent No.: US 9,993,580 B2
(45) Date of Patent: Jun. 12, 2018

(54) PRODUCTS COMPRISING AN EXTRACELLULAR MATRIX TISSUE MATERIAL AND OSTEOGENIC PROTEIN

(71) Applicant: Muffin Incorporated, West Lafayette, IN (US)

(72) Inventors: Shelley Lynn Scoville, Athens, GA (US); Amanda F. Taylor, West Lafayette, IN (US); Steven Charlebois, West Lafayette, IN (US); Christine M. Steinhart, Ramona, CA (US); Neal E. Fearnot, West Lafayette, IN (US)

(73) Assignee: Muffin Incorporated, West Lafayette, IN (US)

( * ) Notice: Subject to any disclaimer, the term of this patent is extended or adjusted under 35 U.S.C. 154(b) by 0 days. days.

(21) Appl. No.: 15/058,329

(22) Filed: Mar. 2, 2016

(65) Prior Publication Data

US 2016/0263282 A1 Sep. 15, 2016

Related U.S. Application Data

(63) Continuation of application No. PCT/US2014/053671, filed on Sep. 2, 2014.

(60) Provisional application No. 61/872,827, filed on Sep. 2, 2013.

(51) Int. Cl.
 *C07K 9/00* (2006.01)
 *A61L 27/36* (2006.01)
 *A61L 27/54* (2006.01)
 *A61L 27/12* (2006.01)

(52) U.S. Cl.
 CPC .......... *A61L 27/3633* (2013.01); *A61L 27/12* (2013.01); *A61L 27/54* (2013.01); *A61L 2300/414* (2013.01); *A61L 2400/06* (2013.01); *A61L 2430/02* (2013.01)

(58) Field of Classification Search
 None
 See application file for complete search history.

(56) References Cited

U.S. PATENT DOCUMENTS

| | | |
|---|---|---|
| 6,180,606 B1 | 1/2001 | Chen et al. |
| 6,206,957 B1 | 3/2001 | Driessens et al. |
| 8,435,552 B2 | 5/2013 | O'Brien et al. |
| 2007/0191963 A1 | 8/2007 | Winterbottom et al. |
| 2008/0274184 A1 | 11/2008 | Hunt |
| 2011/0230406 A1* | 9/2011 | Kehoe ............. A61K 47/48292 514/8.8 |

FOREIGN PATENT DOCUMENTS

| | | |
|---|---|---|
| EP | 1 312 383 | 5/2003 |
| WO | WO 2005/097219 A2 | 10/2005 |
| WO | WO 2009/114535 A2 | 9/2009 |
| WO | WO 2015/031809 A1 | 3/2015 |

OTHER PUBLICATIONS

Ruppert Hugh-Fulford Journal of Orthopedic Surgery and Research, 2011, 6:8.*
Voytik-Harbin Tissue Engineering, vol. 4, No. 2, 1998.*
International Search Report and Written Opinion issued in PCT/US2014/053671, dated Dec. 11, 2014, 17 pgs.
Lutolf, M. P. et al., "Repair of Bone Defects Using Synthetic Mimetics of Collagenous Extracellular Matrices," Nature Biotechnology, 2003, vol. 21, pp. 513-518.
Ruppert, R., et al., "Human Bone Morphogentic Protein 2 Contains a Heparin-Binding Site which Modifies its Biological Activity," European Journal of Biochemistry, 1996, vol. 237, pp. 295-302.
Vejlens, Lars, "Glycosaminoglycans of Human Bone Tissue," Calc Tiss, Res. 7 (1971), pp. 175-190.

* cited by examiner

*Primary Examiner* — Jeanette M Lieb
(74) *Attorney, Agent, or Firm* — Woodard, Emhardt, Moriarty, McNett & Henry LLP

(57) ABSTRACT

Osteogenic compositions include a decellularized extracellular matrix tissue and bone morphogenic protein, preferably BMP-2. The compositions make beneficial use of the BMP, which can be used at relatively low doses and can bind to native components (e.g., native sulfated glycosaminoglycans such as heparin and/or heparan sulfate) remaining in the decellularized extracellular matrix tissue. Methods for preparation and use of such compositions are also described. The compositions and related methods can be used in the treatment of diseased or damaged bone tissue.

22 Claims, 1 Drawing Sheet

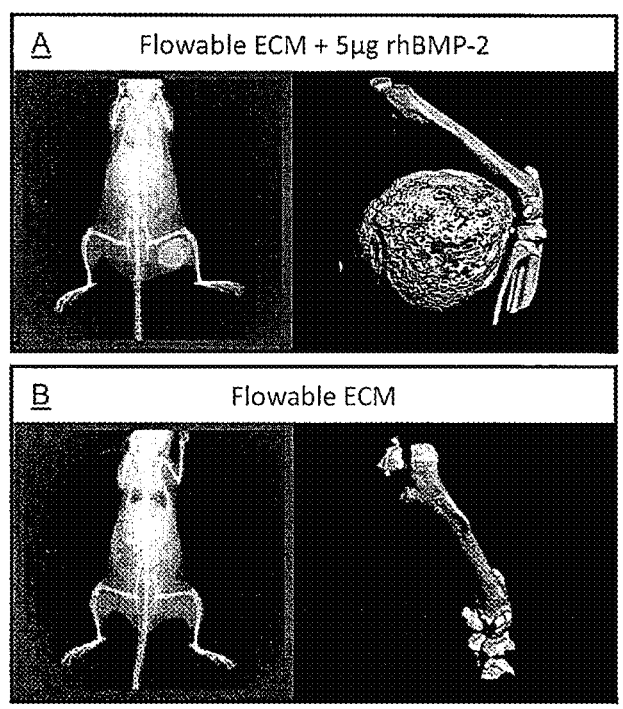

PRODUCTS COMPRISING AN EXTRACELLULAR MATRIX TISSUE MATERIAL AND OSTEOGENIC PROTEIN

REFERENCE TO RELATED APPLICATION

This application is a continuation of International Application No. PCT/US2014/053671, filed Sep. 2, 2014, which claims the benefit of priority of U.S. patent application Ser. No. 61/872,827 filed Sep. 2, 2013 and entitled Products Comprising An Extracellular Matrix Material and Osteogenic Protein, which is hereby incorporated herein by reference in its entirety.

BACKGROUND

The present disclosure pertains to therapeutic compositions and, in certain forms, to osteogenic compositions that include a combination of extracellular matrix tissue material and bone morphogenic protein.

Many medical procedures today rely on regenerating bone, which has become deteriorated as a result of a disease or age or has been damaged (e.g., fractured). While a variety of surgical procedures are available, the advancement of modern medicine has allowed for certain techniques to augment, and sometimes even substitute for these surgeries. For example, a number of genetic factors have been identified, which can serve this purpose if delivered to the correct site. While the concept seems easy to perform, may problems remain.

It is generally known that successful delivery of therapeutic factors e.g., osteogenic factors for endochondral bone formation requires association of the proteins with a carrier. Currently, there are a number of carriers identified in the prior art, all of which have their limitations. For example, carriers include organic substances, such as demineralized bone matrix, non-collagenous proteins, collagen (e.g., collagen sponge), fibrin, autolyzed antigen extracted allogenic bone (AAA-bone), polyglycolic acid, polylactic acid, hydrogels, as well as inorganic materials, such as hydroxyapatite, tricalcium phosphate, other bioceramics, bioactive glass, metals, coral, coral-collagen composite, natural bone mineral, chitin, thermoashed bone mineral, non-demineralized bone particles, ceramic bone particles, ceramic dentin, polyphosphate polymer, irradiated cancellous bone chips, calcium sulfate, and sintered bone. Although these materials are somewhat effective in delivering a therapeutic factor to a desired tissue, they have their limitations. For example, some delivery vehicles fail to retain the therapeutic factor locally for a sufficient period of time. Other delivery vehicles fail to resorb well in the host in which they are administered. Still other delivery vehicles and compositions containing them are lacking in cooperative interaction among the osteogenic factor and the carrier, to enhance tissue formation.

In view of this background, needs remain for improved or alternative osteogenic compositions that can make highly beneficial use of an osteogenic factor, and related methods of use and preparation.

SUMMARY

It has been discovered that extracellular matrix tissue materials can serve has highly beneficial carriers or cooperative components when used with an osteogenic factor to generate hard tissue such as bone. The extracellular matrix tissue materials can serve to advantageously bind the osteogenic factor and in preferred forms contribute additional bioactivity supportive of tissue formation due to the presence of retained native bioactive substances from a source tissue for the extracellular matrix tissue material.

In certain aspects, provided are osteogenic compositions that include a collagenous extracellular matrix tissue material and bone morphogenic protein. Preferred compositional forms are provided where the collagenous extracellular matrix tissue material is a solid matrix, and where the bone morphogenic protein is carried by the solid matrix. The collagenous extracellular matrix tissue material can retain native heparin, heparan sulfate and/or other native components from a source tissue for the collagenous extracellular matrix tissue material, and at least a portion of the bone morphogenic protein can be bound to the native heparin, heparan sulfate, and/or other native components. The bone morphogenic protein can be or comprise any human bone morphogenic protein, preferably: BMP-2, BMP-4, BMP-5, BMP-6, BMP-7, and/or BMP-9, even more preferably BMP-2. In some forms, the bone morphogenic protein comprises a recombinant human bone morphogenic protein, for example BMP-2 ("rhBMP-2"). The BMP-2 and/or other bone morphogenic protein can be provided at a relatively low loading in the composition, for example being present at a level in the range of about 75 μg to about 300 μg per gram, and/or about 25 μg to about 100 μg per cubic centimeter, of the collagenous extracellular matrix tissue material; and/or being present at a total dose of about 6 mg or less, about 4 mg or less, or about 3 mg or less, for example in the range of about 1 to 6 mg or about 1 to 4 mg. Compositions containing such a level and/or total dose of rhBMP-2 or other BMP can be for use in a human patient. The composition can be provided in a non-flowable solid implant form or a flowable (e.g., injectable) form, and in such flowable forms can include an extracellular matrix tissue particulate material and/or a collagenous extracellular matrix gel including a mixture of solubilized extracellular matrix components native to the source tissue. In certain aspects, the composition can also include other bioactive or matrix materials, for example a mineral scaffold material such as a calcium-containing compound.

In certain aspects, provided are osteogenic compositions that include a collagenous extracellular matrix tissue material, a bone morphogenic protein, and erythropoietin (EPO). Preferred compositional forms are provided where the collagenous extracellular matrix tissue material is a solid matrix, and where the bone morphogenic protein is carried by the solid matrix. The collagenous extracellular matrix tissue material can retain native heparin, heparan sulfate and/or other native components from a source tissue for the collagenous extracellular matrix tissue material, and at least a portion of the bone morphogenic protein can be bound to the native heparin, heparan sulfate and/or other native components. The bone morphogenic protein can be or comprise any human bone morphogenic protein, preferably: BMP-2, BMP-4, BMP-5, BMP-6, BMP-7, and/or BMP-9, even more preferably BMP-2. In some forms, the bone morphogenic protein comprises a recombinant human bone morphogenic protein, for example BMP-2 ("rhBMP-2"). The BMP-2 and/or other bone morphogenic protein can be provided at a relatively low loading in the composition, for example being present at a level in the range of about 0.1 μg to about 3 μg per gram, or about 0.1 μg to about 1.5 μg per gram, of the collagenous extracellular matrix tissue material; and/or being present at a total dose of about 6 mg or less, about 4 mg or less, or about 3 mg or less, for example in the range of about 1 to 6 mg or about 1 to 4 mg. Compositions containing such a level and/or total dose of rhBMP-2 or other BMP can be for use in a human patient. In some forms, the EPO comprises a recombinant erythropoietin (rEPO), in certain embodiments the rEPO comprises recombinant human erythropoietin (rhEPO). The composition can be provided in a non-flowable solid implant form or a flowable (e.g., injectable) form, and in such flowable forms can include an extracellular matrix tissue particulate material and/or a collagenous extracellular matrix gel including a mixture of solubilized extracellular matrix components native to the source tissue. In certain aspects, the composition can also include other bioactive or matrix materials, for example a mineral scaffold material such as a calcium-containing compound.

Additional features regarding the components of osteogenic compositions, including but not limited to their identities, levels, ratios, and manner of combination or incorporation in the osteogenic compositions, are provided in the discussions below. It will be understood that these additional features, alone or in combination, can be combined with the features described in the paragraphs above, or elsewhere herein, to form additional embodiments disclosed herein.

Further embodiments disclosed herein relate to methods of use of osteogenic compositions as disclosed herein. These methods can be for the formation of hard tissue such as bone, which can be for the purpose of treating diseased or damaged bone (e.g., for therapeutic or prophylactic treatment).

Still further embodiments disclosed herein relate to methods of preparation of osteogenic compositions as disclosed herein.

Additional embodiments, as well as features and advantages thereof, will be apparent to those skilled in the field upon reviewing the following descriptions.

BRIEF DESCRIPTION OF THE FIGURE

FIG. 1 shows digital images of X-ray and microCT images of NOD/SCID mice 2 weeks after injecting the right thigh muscle with either flowable ECM containing 5 µg rhBMP-2 (FIG. 1,A) or flowable ECM alone (FIG. 1,B), as described further in Example 2 below. Mice receiving injections of a flowable ECM containing 5 µg rhBMP-2 showed abundant, de novo bone formation within the thigh muscle (FIG. 1,A). Animals injected with flowable ECM alone displayed no detectable ectopic bone formation at 2 weeks post injection (FIG. 1,B).

DETAILED DESCRIPTION

Reference will now be made to certain embodiments, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, certain aspects of the present invention relate to osteogenic compositions including bone morphogenic protein, erythropoietin, and extracellular matrix tissue material, and to methods for preparation or use of such compositions.

A variety of osteogenic bone morphogenic proteins are known and can be used in embodiments herein either alone or in combinations of bone morphogenic proteins. Recombinant human bone morphogenetic proteins (rhBMPs) are preferred. Most preferably, the bone morphogenetic protein is rhBMP-2, rhBMP-4, or a heterodimer thereof. rhBMP-2 and rhBMP-7 are commercially available and such commercial forms can be used herein. The bone morphogenic protein can be or comprise any bone morphogenic protein, preferably: BMP-2, BMP-4, BMP-5, BMP-6, BMP-7, and/or BMP-9, even more preferably BMP-2. In some forms, the bone morphogenic protein comprises a recombinant human bone morphogenic protein, for example BMP-2 ("rhBMP-2"). These or other rhBMPs may also be prepared using materials and methods known to those skilled in the art, for example as described in U.S. Pat. Nos. 5,187,076; 5,366,875; 5,108,922; 5,116,738; 5,013,649; 6,352,972 and International PCT Applications WO93/00432; WO94/26893; WO94/26892. The bone morphogenic protein(s) may be provided as a freeze-dried powder, which can be reconstituted during product manufacture or intra-operatively in sterile water for injection or another liquid vehicle for administration or otherwise as a part of manufacture of a composition herein.

Erythropoietin (EPO) is a hormone produced by the kidney and liver in response to hypoxia. EPO binds to the EPO receptor (EpoR) to increase red blood cell production, increase VEGF expression, and stimulate angiogenesis. EPO has also been demonstrated to induce a bone remodeling response through direct stimulation of mesenchymal stem cells and/or bone marrow stromal cells (e.g., by increasing osteoblastogenesis). EPO may indirectly further induce a bone remodeling response by increasing the number of hematopoietic progenitor cells (e.g., increasing osteoclastogenesis). In addition EPO has been shown to induce BMP production by hematopoietic stem cells. The EPO for use in the present invention can be native or recombinant forms of human EPO (rhEPO).

Accordingly, in certain aspects, compositions of the present disclosure include an ECM, a BMP, and EPO. The EPO can be effective to stimulate new blood vessel formation and/or to stimulate the recruitment of mesenchymal stem cells (MSC) to the implant site, and the BMP can be effective to promote the development of osteogenic cells from the mesenchymal stem cells.

The collagenous extracellular matrix (ECM) material used herein can be a decellularized animal tissue layer including ECM tissue. In this regard, "decellularized" as used herein refers to a state of the ECM tissue in which all or substantially all of the cells native to the ECM tissue have been removed; thus, other (non-native) cells can be present on or in the ECM tissue, which is nonetheless referred to as decellularized. The ECM tissue layer can be obtained from a source tissue of a warm-blooded vertebrate animal, such as an ovine, bovine or porcine animal. The source tissue layer is preferably a nonmineralized (i.e. soft tissue) source tissue. For example, suitable ECM tissue include those comprising submucosa, renal capsule membrane, dermal collagen, dura mater, pericardium, amnion, abdominal fascia, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. ECM tissues comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. Porcine tissue sources are preferred sources from which to harvest ECM tissues, including submucosa-containing ECM tissues.

ECM tissue used in the invention is preferably decellularized and highly purified, for example, as described in U.S. Pat. No. 6,206,931 to Cook et al. or U.S. Patent Application Publication No. US2008286268 dated Nov. 20, 2008, publishing U.S. patent application Ser. No. 12/178,321 filed Jul. 23, 2008, all of which are hereby incorporated herein by reference in their entirety. Preferred ECM tissue material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 $\mu$g/mg, more preferably less than about 2 $\mu$g/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 or U.S. Patent Application Publication No. US2008286268 may be characteristic of any ECM tissue used in the present invention.

In certain embodiments, the ECM tissue material used herein will be a membranous tissue with a layer structure as isolated from the tissue source. The ECM tissue can, as isolated, have a layer thickness that ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

The ECM tissue material utilized desirably retains a structural microarchitecture from the source tissue, including structural fiber proteins such as collagen and potentially also elastin that can form native fibers. Such fibers can in certain embodiments be non-randomly oriented, as can occur in the source tissue for the decellularized ECM tissue material. Such non-random collagen and/or other structural protein fibers can in certain embodiments provide an ECM tissue that is non-isotropic in regard to tensile strength, thus having a tensile strength in one direction that differs from the tensile strength in at least one other direction.

The decellularized ECM tissue material may include one or more bioactive agents native to the source of the ECM tissue material and retained in the ECM tissue material through processing. For example, a submucosa or other ECM tissue material may retain one or more native growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bio active agents such as but not limited to proteins, glycoproteins, proteoglycans, and glycosaminoglycans. For example, decellularized ECM tissue materials may include native heparin, heparin sulfate, hyaluronic acid, fibronectin, cytokines, and the like. Thus, generally speaking, a submucosa or other ECM tissue material may retain from the source tissue one or more bioactive components that induce, directly or indirectly, a cellular response such as a change in cell morphology, proliferation, growth, protein or gene expression.

Submucosa-containing ECM materials or other ECM materials used in the present invention can be derived from any suitable organ or other tissue source, usually a soft tissue source (non-bone, non-cartilage) containing connective tissue. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors (e.g., as discussed above), the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa-containing or other ECM tissue material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Decellularized ECM tissue layers can be used in the invention as single layer implants, but in certain embodiments will be used in multilaminate constructs. In this regard, a variety of techniques for laminating layers together are known and can be used to prepare multilaminate constructs used for the graft in the present invention. For example, a plurality of (i.e. two or more) layers of collagenous material, for example submucosa-containing or other ECM material, can be bonded together to form a multilaminate structure. Illustratively, two to about two hundred decellularized collagenous ECM tissue layers can be bonded together to provide a multilaminate construct for use in the present invention. In certain embodiments, two to eight decellularized collagenous ECM tissue layers are bonded together to form a multilaminate construct for use herein. Preferably submucosa-containing ECM tissue layers are isolated from intestinal tissue, more preferably small intestinal tissue. Porcine-derived tissue is preferred for these purposes. The layers of ECM tissue can be bonded together in any suitable fashion, including dehydrothermal bonding under heated, non-heated or lyophilization conditions, using adhesives, glues or other bonding agents, crosslinking with chemical agents or radiation (including UV radiation), or any combination of these with each other or other suitable methods. For additional information as to multilaminate ECM constructs that can be used in the invention, and methods for their preparation, reference may be made for example to U.S. Pat. Nos. 5,711,969, 5,755,791, 5,855,619, 5,955,110, 5,968,096, and to U.S. Patent Publication No. 20050049638 A1 published Mar. 3, 2005. These constructs can be perforated or non-perforated, and when perforated may include an array of perforations extending substantially across the surface of the construct, or may include perforations only in selected areas.

Osteogenic compositions of embodiments herein can incorporate xenograft ECM tissue material (i.e., cross-species material, such as tissue material from a non-human donor to a human recipient), allograft ECM material (i.e., interspecies material, with tissue material from a donor of the same species as the recipient), and/or autograft ECM material (i.e., where the donor and the recipient are the same individual). Further, BMP and/or other exogenous bioactive substances incorporated into an ECM material may be from the same species of animal from which the ECM material was derived (e.g., autologous or allogenic relative to the ECM material) or may be from a different species from the ECM material source (xenogenic relative to the ECM material). In certain embodiments, the ECM tissue material will be xenogenic relative to the patient receiving the graft, and any added cells or other exogenous material(s) will be from the same species (e.g., autologous or allogenic) as the patient receiving the graft. Illustratively, human patients may be treated with xenogenic ECM materials (e.g., porcine-, bovine- or ovine-derived) that have been modified with exogenous human BMP(s) such are rhBMP(s) as described herein.

ECM tissue materials used in embodiments herein can be free or essentially free of additional, non-native crosslinking, or may contain additional crosslinking. Such additional crosslinking may be achieved by photo-crosslinking techniques, by chemical crosslinkers, or by protein crosslinking induced by dehydration or other means. However, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

In additional embodiments, osteogenic compositions herein can incorporate ECM tissue material that has been subjected to a process that expands the tissue material. In certain forms, such expanded materials can be formed by the controlled contact of an ECM material with a denaturing agent such as one or more alkaline substances until the material expands, and the isolation of the expanded material. Illustratively, the contacting can be sufficient to expand the ECM tissue material to at least 120% of (i.e. 1.2 times) its original bulk volume, or in some forms to at least about two times its original volume. Thereafter, the expanded material can optionally be isolated from the alkaline medium (e.g., by neutralization and/or rinsing). The collected, expanded material can be used in any suitable manner in the preparation of a material for administration to a patient. The expanded material can be enriched with bioactive components, comminuted, dried, and/or molded, etc., in the formation of an implantable body of a desired shape or configuration. In certain embodiments, a dried implant body formed with an expanded ECM tissue material can be compressible.

Treatment of an ECM tissue material with a denaturant, such as an alkaline material, can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. It will be apparent to one skilled in the art that the magnitude of the expansion is related to several factors, including for instance the concentration or pH of the alkaline medium, the exposure time of the alkaline medium to the material, and temperature used in the treatment of the material to be expanded, among others. These factors can be varied through routine experimentation to achieve a material having the desired level of expansion, given the disclosures herein.

A collagen fibril is comprised of a quarter-staggered array of tropocollagen molecules. The tropocollagen molecules themselves are formed from three polypeptide chains linked together by covalent intramolecular bonds and hydrogen bonds to form a triple helix. Additionally, covalent intermolecular bonds are formed between different tropocollagen molecules within the collagen fibril. Frequently, multiple collagen fibrils assemble with one another to form collagen fibers. It is believed that the addition of an alkaline substance to the material as described herein can be conducted so as to not significantly disrupt the intramolecular and intermolecular bonds, but denature the material to an extent that provides to the material an increased processed thickness (e.g., at least twice the naturally-occurring thickness). ECM materials that can be processed to make expanded materials for use as substrates can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness. The expanded ECM material can then be processed to provide foam or sponge substrates for use as or in the graft body, e.g. by comminuting, casting, and drying the processed material. Additional information concerning expanded ECM materials and their preparation is found in United States Patent Application Publication No. US20090326577 published Dec. 31, 2009, publishing U.S. patent application Ser. No. 12/489,199 filed Jun. 22, 2009, which is hereby incorporated herein by reference in its entirety.

In certain embodiments herein, the osteogenic composition can consist or consist essentially of the decellularized ECM tissue and the BMP, preferably rhBMP-2. Additionally or alternatively, the osteogenic composition can be predominantly comprised of the decellularized ECM tissue and the BMP, preferably rhBMP-2, for example at least 80% by weight, at least 90% by weight, or at least 95% by weight, on a dry weight basis.

In other forms, in addition to ECM tissue materials, compositions herein can include other organic carrier materials. Illustrative materials include, for example, synthetically-produced substrates comprised or natural or synthetic polymers. Illustrative synthetic polymers are preferably biodegradable synthetic polymers such as polylactic acid, polyglycolic acid or copolymers thereof, polyanhydride, polycaprolactone, polyhydroxy-butyrate valerate, polyhydroxyalkanoate, or another biodegradable polymer or mixture thereof. Preferred implant bodies comprised of these or other materials (e.g., ECM materials as discussed herein) will be porous matrix materials configured to allow cellular invasion and ingrowth into the matrix.

Inorganic scaffolding materials can also be incorporated in the compositions herein. In certain embodiments, the compositions can incorporate one or more mineral-containing materials along with the ECM tissue material and bone morphogenic protein. Such mineral material(s) can serve as scaffolding to support the generation of hard tissue such as bone. Many mineral-containing materials for such purposes are known and can be used, for example in particulate form. Suitable materials include for instance hydroxyapatite, tricalcium phosphate, bioglass, calcium phosphate, calcium sulfate, bone, or combinations thereof.

A mineral-containing material and the ECM tissue material can be combined in any suitable manner. In some variants, the mineral-containing material is a particulate material, such as a powder or granular material, and the ECM tissue material is also a particulate material. In these forms, the mineral-containing particulate and the ECM tissue particulate can be in admixture with one another, preferably in a substantially homogenous admixture. Such admixtures can be provided in dry form for later combination with bone morphogenic protein, or can have bone morphogenic protein in dry (e.g., lyophilized) form included in the admixture. In still other forms, the ECM tissue material can provide an ECM matrix, and particles of the mineral-containing material can be embedded in the ECM matrix; or, the mineral-containing material can provide a mineral matrix, and particles of the ECM tissue material can be embedded in the mineral matrix.

As well, the mineral-containing material and the ECM tissue material can be combined in the form of a mineralized ECM tissue matrix, in which mineral particles are adhered to native structural fibers of the ECM tissue, such as collagen and/or elastin fibers, and/or entrapped between the native structural fibers, and/or entrapped within the native structural fibers. Such a mineralized ECM tissue matrix can be prepared by a method in which the mineral particles are precipitated from solution onto the native structural fibers of the ECM tissue matrix, into the native structural fibers of the ECM tissue matrix, between the native structural fibers of the ECM tissue matrix, or combinations thereof. For example, the mineralization process can include mixing, within the porous matrix of the ECM tissue, a first solution containing solvated ions of a first component of the mineral particles to be formed, and at least a second solution containing solvated ions of a second component of the mineral particles to be formed. The first and second component can thereby interact (e.g., ionically or otherwise) in the formation of the mineral particles of the mineralized ECM tissue matrix. In other preparative modes, the ECM tissue matrix can be alternately contacted with at least the first and second solutions to result in the formation of the mineral particles within the ECM tissue matrix. In certain embodiments the first solution can include dissolved amounts of a soluble calcium salt and the second solution can include dissolved amounts of a soluble phosphate salt, and the resulting precipitated mineral particles can contain calcium and phosphate. Other cationic or anionic species may also be present in the reagent solutions such as carbonate, chloride, fluoride, sodium or ammonium, and the mineral particles can be comprised of calcium hydroxyapatite, calcium hydroxy/fluorapatite, brushite, dahlite, monetite, phosphated calcium carbonate (calcite), octacalcium phosphate, or tricalcium phosphate, as examples. It will be understood that the choice of stoichiometry of the calcium and the phosphate, as well as the presence of other ions, will result in a particular composition for the formed mineral particles. For additional information regarding mineralizing solutions and techniques, reference can be made to U.S. Pat. Nos. 5,455,231, 5,508,267, 6,187,047, 6,384,196 and 6,764,517.

In mineralized ECM tissue materials herein or in other compositions incorporating a mineral scaffolding material, the mineral scaffolding material can constitute any suitable percentage by weight of the overall composition. In certain embodiments, the mineral scaffolding material constitutes about 5% to about 90% by weight, or about 5% to about 60% by weight, or about 5% to about 40% by weight, of the overall composition on a dry weight basis.

Further in regard to mineralized ECM tissue, as discussed above, preferred decellularized ECM tissue materials used herein can retain native bioactive substances from a source tissue for the ECM tissue material. The mineralization of such bioactive ECM tissue materials can be conducted so as to result in an ECM tissue matrix that not only has mineral particles adhered to, within, and/or between the collagen and/or elastin fibers of the ECM tissue, but that also retains amounts of such native bioactive substances from the source tissue, which can include one or more growth factors (e.g., FGF-2), glycosaminoglycans, proteoglycans and/or glycoproteins. As discussed above, these non-collageous native bioactive materials can be present as solids interspersed between collagen fibers of the ECM tissue material. Thus, mineralized ECM tissue materials can in certain forms include native collagen and/or elastin fibers, mineral particles adhered, within and/or between those fibers with mineral particles preferably having maximum cross-sectional dimensions smaller than the fibers, and non-collagen bioactive solids interspersed between the fibers and including one or more growth factors (e.g., FGF-2), glycosaminoglycans, proteoglycans, and/or glycoproteins from the source tissue for the ECM tissue material. Embodiments disclosed herein include those in which such interspersed non-collagen native bioactive solids can constitute at least 1% by weight, or at least 3% by weight, of the ECM tissue material on a dry weight basis (excluding the mineral material).

The ECM tissue material used herein can optionally be in particulate form, for example as incorporated into flowable compositions for administration. Such ECM particulate materials can have particles or random and/or regular shape. Illustratively, random ECM tissue particulates can be prepared by crushing, grinding or chopping a larger decellularized ECM tissue sheet material. On the other hand, a regular ECM tissue particulate can be prepared by controlled cutting of shapes such as circular, ovoid or polygonal shapes from a larger decellularized ECM tissue layer material (e.g., to provide disk form particles). Such regular ECM particles can retain a sheet form, and can in certain embodiments have maximum sheet dimensions (across the face of the sheet particles) in the range of about 0.1 to about 1 mm, or about 0.1 to about 5 mm, or about 0.1 to about 2 mm. In addition or alternatively, the regular ECM particles can be multilaminate constructs containing multiple bonded decellularized ECM layers, for example as can be prepared by controlled cutting, as mentioned above, of corresponding larger multilaminate decellularized ECM tissue constructs. Methods of laminating multiple layers of decellularized ECM layers are described herein and can be used in the generation of the larger multilaminate decellularized ECM tissue constructs to be cut to generate the regular ECM particulate. An ECM particulate can be incorporated with a flowable liquid carrier, typically an aqueous carrier, along with other components herein, to form an injectable or otherwise flowable composition for administration.

The BMP can be combined with a solid ECM tissue in any suitable fashion. For example, the BMP can be dissolved in a liquid carrier such as distilled water or a buffered aqueous solution, and the liquid carrier can be contacted with the ECM tissue. Any suitable period of contact can be used. In certain modes, the ECM tissue and the liquid carrier containing the BMP are contacted with one another for a period of at least 1 minute, at least 5 minutes, or at least 10 minutes, for example in the range of about 5 minutes to 60 minutes. As discussed above, in some embodiments herein, the ECM tissue material will retain native sulfated glycosaminoglycans such as heparin and/or heparan sulfate, and potentially also other native components, from its source tissue. Contact of the liquid carrier with the ECM tissue material over these periods of time can allow the BMP to bind to this native heparin, heparan sulfate and/or other native components. The BMP component(s) may also be modified, encapsulated, or chemically and/or covalently bound to the ECM to promote a longer half-life of biological activity. The contact of the liquid BMP formulation and the ECM tissue can occur at the point of care; alternatively, this can occur during commercial product manufacture, for example where the resulting BMP impregnated ECM tissue material is thereafter lyophilized to form a dry construct, which can be sterilely packaged for storage and later use. In addition, after contact of the liquid BMP formulation with the ECM tissue, in some embodiments, the resulting BMP-impregnated ECM tissue can be rinsed with water or another appropriate rinse liquid to remove at least some of the unbound BMP from the composition, and in certain aspects to remove at least 70% of the unbound BMP. This can provide a composition in which a predominant amount of the BMP administered to the patient is bound to the carrier material and thus more effectively localized to the implant site.

The ECM tissue matrix and BMP can also be combined in a flowable implant composition. For these purposes, the ECM tissue can be in particulate and/or gel form. The flowable carrier material in such compositions can include a gel form of the ECM tissue and/or another material, and will typically be an aqueous carrier material. The flowable carrier in some embodiments can be or include an inorganic flowable carrier, for instance a hardenable inorganic flowable carrier such as a paste that is settable to form a calcium phosphate-containing or calcium sulfate-containing cement. Illustratively, reactants that include a calcium source and a phosphate source can be combined with the ECM tissue material in particulate and/or gel form, and the BMP, to produce a flowable composition that sets into a non-flowable calcium phosphate solid. The calcium source and phosphate source may be present as a single compound or present as two or more compounds. As such, a single calcium phosphate present in the dry reactants may be the calcium source and the phosphate source. Alternatively, two or more compounds may be present in the dry reactants, where the compounds may be compounds that include calcium, phosphate or calcium and phosphate. Calcium phosphate sources of interest that may be present in the dry reactants include: MCPM (monocalcium phosphate monohydrate or $Ca(H_2PO_4)_2.H_2O$); DCPD (dicalcium phosphate dihydrate, brushite or $CaHPO_4.2H_2O$), ACP (amorphous calcium phosphate or $Ca_3(PO_4)_2H_2O$), DCP (dicalcium phosphate, monetite or $CaHPO_4$), tricalcium phosphate, including both .alpha.- and .beta.- $(Ca_3(PO_4)_2$, tetracalcium phosphate $(Ca_4(PO_4)_{2O}$, etc. Calcium sources of interest include: calcium carbonate ($CaCO_3$), calcium oxide (CaO), calcium hydroxide ($Ca(OH)_2$ and the like. Phosphate sources of interest include: Phosphoric acid ($H_3PO_4$), soluble phosphate salts, and the like. In certain forms, the above calcium containing and phosphorous containing reactants can be in dry form (e.g., with ECM tissue particles admixed therewith) and these dry reactants can be combined with a liquid medium, for example distilled water, an aqueous acid solution (e.g., phosphoric acid), or an aqueous solution containing a soluble orthophosphate or monocalcium phosphate monohydrate, to form a flowable, settable composition. The settable composition can set, as examples, to a non-stoichiometric calcium-deficient hydroxyapatite or brushite material. This set material can entrain the particulate and/or gel form ECM tissue material. As well, the BMP in such settable compositions, or set materials, can be bound to the ECM tissue material (e.g., through binding to native sulfated glycosaminoglycans such as heparin and/or heparan sulfate and/or other native components therein), included within the flowable carrier and resulting set inorganic matrix material, or a combination thereof. In certain forms, at least 50%, at least 70%, or at least 90% by weight of the BMP will be bound to the ECM tissue material in solid carrier form (e.g., particulate form), which will thus be enriched in the BMP as compared to the flowable liquid carrier material of the composition.

The BMP can be incorporated into the flowable composition using any suitable technique. It can be impregnated into the ECM tissue material, which can then be incorporated into the flowable composition (e.g., by suspension or mixture with an aqueous medium or other flowable carrier material). Alternatively or in addition, the BMP can be incorporated into a liquid medium to serve as the flowable carrier medium or at least a portion thereof, and this liquid medium can then be combined with the ECM tissue material. Still further, the BMP in dry powder (e.g., lyophilized) form can be combined with the ECM material in dry form, to form a dry mixture. This dry mixture can then be combined with a liquid medium to form the flowable composition. These and other modes of preparation of the flowable composition including the ECM tissue material and the BMP will be apparent to those skilled in the pertinent field from the descriptions herein. Likewise, kits containing these components in separately packaged form, for combination to prepare a flowable composition, for example at the point of care, provide additional embodiments herein.

In compositions herein, the BMP-2 and/or other BMP can be provided at a relatively low loading in the composition and/or used at a relatively low dose in the patient. For example, the BMP-2 or other BMP can be present at a level in the range of about 75 to about 300 micrograms per gram of the collagenous extracellular matrix tissue material in the composition (dry weight basis), at a level in the range of about 25 to about 300 micrograms per cubic centimeter of the collagenous extracellular matrix tissue material in the composition, and/or at a total BMP-2 or other BMP dose of about 4 mg or less or about 3 mg or less, for example in the range of about 1 to 4 mg. These values for loading and dosing can be used when the patient is human.

In some forms, the present disclosure includes a method for preparing an osteogenic composition comprising saturating a collagenous extracellular matrix tissue material in a solution containing BMP. In accordance with certain inventive variants, the solution comprises about 0.1 µg/ml BMP to about 10 µg/ml BMP. In preferred embodiments the solution comprises about 0.1 µg/ml BMP to about 1 µg/ml BMP.

As disclosed above, in some embodiments, the compositions containing ECM and BMP will also include EPO. In this regard, the EPO can be combined with the ECM together with, or separately from, the BMP. For example, a liquid medium (e.g., solution) containing both the EPO and BMP can be combined with the ECM in certain embodiments. In others, separate solutions or other liquid media containing, respectively, the BMP and the EPO, can be combined with the ECM. As disclosed above, EPO can be present in an amount effective to stimulate new blood vessel formation and/or to stimulate the recruitment of mesenchymal stem cells (MSC) to the implant site. In conjunction therewith, the BMP can be effective to promote the development of osteogenic cells from mesenchymal stem cells. The EPO, when used, can be native or recombinant form of human EPO (rhEPO).

The compositions disclosed herein may also be seeded with cells, which can in some forms be autologous or allogenic to the recipient of the composition. The cells employed may be primary cells, explants, or cell lines, and may be dividing or non-dividing cells. Cells may be expanded ex-vivo prior to introduction into the inventive cement compositions. Autologous cells are preferably expanded in this way if a sufficient number of viable cells cannot be harvested from the host. The cells may be non-genetically engineered (not having been subjected to introduction of genetic material to genetically alter the cells), or may be genetically engineered, for example to produce a protein or other factor that it useful in a particular application. The cells may be combined into the compositions herein during preparation (before administration to a patient) or may be administered to the patient separately from the compositions herein so as to seed the administered composition in situ in the patient.

The compositions disclosed herein can be used in a variety of applications. In preferred uses, the compositions are used in the treatment of skeletal defects such as diseased or damaged bone or other defects that require bone growth, for example to fuse adjacent vertebrae. For example, the diseased or damaged bone can occur in any of the bones in an animal, especially a mammal such as a human, including flat bones (e.g., ribs and the frontal and parietal bones of the cranium), long bones (e.g., bones of the extremities), short bones (e.g., wrist and ankles bones), irregular bones (e.g., vertebrae and the pelvis), and sesamoid bones (e.g., the patella). Damaged bone to be treated can include fractured bone. Diseased bone to be treated can in some embodiments include osteopenic bone, osteoporotic bone, or necrotic bone. Combined diseased and damaged bone can also be treated, for example in the case of fractured osteopenic bone or fractured osteoporotic bone. The fusion of adjacent vertebrae can involve the implantation of compositions disclosed herein between first and second adjacent vertebral bodies, potentially in combination with one or more fusion cages or other spacer implants configured to support the vertebral bodies in spaced condition from one another.

For the purpose of promoting a further understanding of embodiments herein and features and advantages thereof, the following specific Examples are provided. It will be understood that these Examples are illustrative, and not limiting, of the scope of embodiments otherwise described herein.

EXAMPLE 1

Preparation of 1 µg BMP-2 samples rhBMP-2 was obtained from −20° C. freezer. A 4 mM solution of HCl in water was made up and sterilized by passing it through a 0.2 µm syringe filter. 100 µl of the 4 mM HCl solution was added to the BMP-2 vial making a 100 µg/ml solution. The solution was briefly spun in a microfuge. A 10 µl (1 µg) aliquot was placed into a sterile tube and stored at −20° until day of implant.

Preparation of 0.3 µg BMP-2 samples rhBMP-2 was obtained from −20° C. freezer. A 4 mM solution of HCl in water was made up and sterilized by passing it through a 0.2 µm syringe filter. 100 µl of the 4 mM HCl solution was added to the BMP-2 vial making a 100 µg/ml solution. The solution was briefly spun in a microfuge. A 30 µl/ml solution was made by adding 30 µl of the rhBMP-2 solution and 70 µl of the 4 mM HCl. The 30 µl/ml solution was briefly spun in the microfuge. A 10 µl (0.3 µg) aliquot was placed into a sterile tube and stored at −20° until day of implant.

Preparation of 0.1 µg BMP-2 samples rhBMP-2 was obtained from −20° C. freezer. A 4 mM solution of HCl in water was made up and sterilized by passing it through a 0.2 µm syringe filter. 100 µl of the 4 mM HCl solution was added to the BMP-2 vial making a 100 µg/ml solution. The solution was briefly spun in a microfuge. A 10 µl/ml solution was made by adding 10 µl of the rhBMP-2 solution and 90 µl of the 4 mM HCl. The 10 µl/ml solution was briefly spun in the microfuge. A 10 µl (0.1 µg) aliquot was placed into a sterile tube and stored at −20° until day of implant.

Implant Preparation and surgery A 4 mm diameter disk was cut from an ECM sheet material (a 4-layer laminate of renal capsule, "RC") with a 4-mm biopsy punch. The RC disk implant was added to a 10 µl aliquot of rhBMP-2 solution prepared as described in this Example above, ensuring the sheet was fully saturated in the solution. The vial with the saturated RC disk implant was placed in an incubator at 37° C. for a minimum of 30 minutes. The hydrated RC disk was removed from the vial, and then passed into the surgical field to allow the surgeon to implant into a prepared defect of a known immunodeficient (SCID) mouse calvarial defect model. For the model, bilateral 4 mm diameter defects were drilled in each mouse. One of the bilateral defects was used as a control (receiving no treatment material) and the other received the treatment material. Two lengths of titanium wire were tied to the outer edge of the implant disc on opposed sides as imageable references. Sutures were routed through cranial and caudal suture holes drilled in the treatment defects and through mated holes in the implant disk. The implant disk was secured to parietal bone with a suture knot. Control (void) treatment sites were similarly tied with sutures but received no implant. The incisions were closed, and the mouse was fitted with an Elizabethan collar (worn for 1 week after surgery). The mice in the study were imaged in vivo with microCT (small scale computed tomography) at 2, 4, 8, and 12 weeks post implant. The microCT scans were used the change in bone coverage for the treated and untreated defects.

Results: For defects treated with the ECM implant disks soaked in the 1, 0.3 and 0.1 microgram solutions the percent bone coverage at 12 weeks post implant averaged 88.8% (n=7), 87.1% (n=6) and 68.5% (n=7), respectively. For the corresponding untreated defects in these groups, the percent bone coverage at 12 weeks post implant averaged 19.5%, 18.6% and 24.5% (n=7), respectively. Also, in experiments similarly conducted but carried out to 16 weeks instead of 12 weeks, a group of mice (n=7) receiving just the ECM implant disk (no added rhBMP-2) on one side and no treatment on the other side averaged about 35% bone coverage on the treated side and about 22% bone coverage on the untreated side at 16 weeks post implant.

EXAMPLE 2

Preparation of 10 μg rhBMP-2 samples rhBMP-2 was obtained from −20° C. freezer. A 4 mM solution of HCl in water was made up and sterilized by passing it through a 0.2 μm syringe filter. 500 μl of the 4 mM HCl solution was added to the BMP-2 vial making a 100 μg/mL solution. The solution was briefly spun in a microfuge. A 100 μl (10 μg) aliquot was placed into a sterile tube and stored at −80° C. until day of implant.

Implant Preparation and Surgery: A flowable implant composition of ECM material was produced by rehydrating micronized small intestine submucosa, (SIS) in PBS. The rehydrated, flowable ECM formulation was mixed well, and 100 μl was transferred to a sterile syringe and connected to a second syringe containing the 100 μl aliquot of rhBMP-2 solution prepared as described in this Example above. The rehydrated, flowable ECM formulation and rhBMP-2 were mixed together using a syringe connector and then placed in an incubator at 37° C. for a minimum of 30 minutes.

The rehydrated, flowable ECM containing rhBMP-2 was removed from the incubator and then passed into the surgical field. Formulations were briefly mixed, and 100 μl of the rehydrated, flowable ECM containing approximately 5 μg of rhBMP-2 was transferred to a sterile syringe and promptly injected through a 23 G needle into the hind thigh muscle of a known immunodeficient (NOD/SCID) mouse model of ectopic bone formation. Control (negative) treatments were prepared and injected into the thigh muscle as described in the example above with the exception that the rehydrated, flowable ECM formulation was mixed with 100 μl of PBS. Post injection mice were recovered and returned to the housing unit. The mice in the study were imaged in vivo with x-ray at 1 and 2 weeks post injection. The x-rays were used to detect de novo bone formation in the thigh muscle. The mice in the study were sacrificed at 2 weeks post injection and imaged ex vivo with micro-computed tomography (microCT). The microCT scans were used to image and quantify de novo bone formation in the thigh muscle.

Results: Mice treated with the flowable ECM containing 5 μg rhBMP-2 showed abundant de novo bone formation within the thigh muscle at 2 weeks post injection (FIG. 1,A). Control animals that received an injection of 100 μl of flowable ECM exhibited no intramuscular bone formation at 2 weeks follow-up (FIG. 1,B).

As used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs.

Where a range of values is provided, it is understood that each intervening value, to the tenth of the unit of the lower limit, unless the context clearly dictates otherwise, between the upper and lower limit of that range and any other stated or intervening value in that stated range, is encompassed within the invention. The upper and lower limits of these smaller ranges may independently be included in the smaller ranges, and such embodiments are also encompassed within the invention, subject to any specifically excluded limit in the stated range. Where the stated range includes one or both of the limits, ranges excluding either or both of those included limits are also included in the invention.

All publications mentioned herein are incorporated herein by reference for the purpose of describing and disclosing components that are described in the publications that might be used in connection with the presently described invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all publications cited herein are indicative of the abilities of those of ordinary skill in the art and are hereby incorporated by reference in their entirety as if individually incorporated by reference and fully set forth.

What is claimed is:

1. A method for preparing an osteogenic composition, comprising:
    combining bone morphogenic protein and a collagenous extracellular matrix tissue material, wherein the collagenous extracellular matrix tissue material includes native heparin, heparan sulfate and/or other native components from a source tissue for the collagenous extracellular matrix tissue material, and wherein said combining results in binding of the bone morphogenic protein to the native heparin, heparan sulfate and/or other native components, and wherein said combining is performed such that bone morphogenic protein is present at a level of 75 to 300 micrograms per gram of the collagenous extracellular matrix tissue material on a dry weight basis.

2. The method of claim 1, wherein the collagenous extracellular matrix tissue material includes native heparin from a source tissue for the collagenous extracellular matrix tissue material, and wherein said combining results in binding of the bone morphogenic protein to the native heparin.

3. The method of claim 1, wherein the bone morphogenic protein comprises recombinant human BMP-2 and/or wherein the bone morphogenic protein is constituted at least 95% by weight of recombinant human BMP-2.

4. The method of claim 1, wherein the collagenous extracellular matrix tissue material retains native growth factors, glycosaminoglycans, proteoglycans and glycoproteins from a source tissue for the extracellular matrix tissue material.

5. The method of claim 1, wherein the collagenous extracellular matrix tissue material retains native FGF-2 from a source tissue for the extracellular matrix tissue material.

6. The method of claim 5, wherein the native FGF-2 is present in the collagenous extracellular matrix tissue material at a level of at least about 50 nanograms per gram of the collagenous extracellular matrix tissue material.

7. The method of claim 1, wherein the collagenous extracellular matrix tissue material comprises submucosal tissue.

8. The method of claim 1, wherein the collagenous extracellular matrix tissue material is a porcine collagenous extracellular matrix tissue material.

9. The method of claim 1, also comprising incorporating a calcium phosphate compound in the composition.

10. The method of claim 9, wherein the calcium phosphate compound includes hydroxyapatite, tricalcium phosphate, or a combination thereof.

11. The method of claim 1, wherein said combining results in an amount of the bone morphogenic that is bound to native heparin in the extracellular matrix tissue material and an amount of the bone morphogenic protein impregnated in the extracellular matrix tissue material but unbound to native heparin in the extracellular matrix tissue material.

12. The method of claim 11, also comprising removing at least a portion of said amount of bone morphogenic protein that is impregnated in the extracellular matrix tissue material but unbound to native heparin in the extracellular matrix tissue material.

13. The method of claim 12, wherein said removing is conducted so as to remove at least 90% of said amount of bone morphogenic protein that is impregnated in the extracellular matrix tissue material but unbound to native heparin the extracellular matrix tissue material.

14. The method of claim 12, wherein said removing comprises rinsing the extracellular matrix tissue material with an aqueous medium.

15. The method of claim 1, wherein said combining results in an amount of the bone morphogenic that is bound to native heparin, heparan sulfate and/or other native components in the extracellular matrix tissue material and an amount of the bone morphogenic protein impregnated in the extracellular matrix tissue material but unbound to native heparin, heparan sulfate and/or other native components in the extracellular matrix tissue material.

16. The method of claim 15, also comprising removing at least a portion of said amount of bone morphogenic protein that is impregnated in the extracellular matrix tissue material but unbound to native heparin, heparan sulfate and/or other native components in the extracellular matrix tissue material.

17. The method of claim 16, wherein said removing is conducted so as to remove at least 90% of said amount of bone morphogenic protein that is impregnated in the extracellular matrix tissue material but unbound to native heparin, heparan sulfate and/or other native components in the extracellular matrix tissue material.

18. The method of claim 16, wherein said removing comprises rinsing the extracellular matrix tissue material with an aqueous medium.

19. The method of claim 1 wherein said combining comprises the step of:
contacting the collagenous extracellular matrix tissue material with a liquid carrier containing the bone morphogenic protein.

20. The method of claim 19 wherein the liquid carrier comprises 0.1 µg/ml BMP to 10 µg/ml BMP.

21. The method of claim 19 further comprising:
lyophilizing the bone morphogenic protein and the collagenous extracellular matrix tissue material after said contacting to form a dry construct.

22. The method of claim 1, wherein said combining is performed such that bone morphogenic protein is present at a level of 25 to 300 micrograms per cubic centimeter of the collagenous extracellular matrix tissue material on a dry weight basis.

* * * * *